(12) United States Patent
Lin et al.

(10) Patent No.: US 8,703,944 B2
(45) Date of Patent: Apr. 22, 2014

(54) METHOD FOR PREPARING ROSUVASTATIN CALCIUM INTERMEDIATE

(71) Applicant: Porton Fine Chemicals Ltd., Chongqing (CN)

(72) Inventors: Wenqing Lin, Chongqing (CN); Hongjie Zheng, Chongqing (CN); Peng Yang, Chongqing (CN)

(73) Assignee: Porton Fine Chemicals Ltd., Chongqing (CN)

( * ) Notice: Subject to any disclaimer, the term of this patent is extended or adjusted under 35 U.S.C. 154(b) by 0 days.

(21) Appl. No.: 13/757,846

(22) Filed: Feb. 3, 2013

(65) Prior Publication Data

US 2013/0143908 A1    Jun. 6, 2013

Related U.S. Application Data

(63) Continuation-in-part of application No. PCT/CN2011/075757, filed on Jun. 15, 2011.

(30) Foreign Application Priority Data

Aug. 4, 2010 (CN) .......................... 2010 1 0244963

(51) Int. Cl.
*C07D 239/02* (2006.01)
*C07D 239/42* (2006.01)

(52) U.S. Cl.
USPC ............ 544/297; 544/322; 544/330; 544/332

(58) Field of Classification Search
USPC .......................................... 544/297, 322, 330
See application file for complete search history.

(56) References Cited

U.S. PATENT DOCUMENTS 5,260,440 A * 11/1993 Hirai et al. ..................... 544/332
8,476,432 B2 * 7/2013 Ju et al. ......................... 544/297
2007/0043037 A1 * 2/2007 Aranyi et al. ................ 514/227.5

FOREIGN PATENT DOCUMENTS

WO    WO03097614 A2 * 11/2003 ........... C07D 293/00
WO    WO2008059519 A2 * 5/2008 ........... C07D 239/42

* cited by examiner

*Primary Examiner* — Paul Zarek
*Assistant Examiner* — George W Kosturko
(74) *Attorney, Agent, or Firm* — Matthias Scholl P.C.; Matthias Scholl

(57) ABSTRACT

A method for preparing a rosuvastatin calcium intermediate represented by formula I. The method includes: hydrolyzing an ester compound represented by formula II (in which, R represents C1-C5) in the presence of a metal compound to obtain a carboxylic acid compound represented by formula III; and reducing the carboxylic acid compound in the presence of a reductant.

5 Claims, No Drawings

METHOD FOR PREPARING ROSUVASTATIN CALCIUM INTERMEDIATE

CROSS-REFERENCE TO RELATED APPLICATIONS

This application is a continuation-in-part of International Patent Application No. PCT/CN2011/075757 with an international filing date of Jun. 15, 2011, designating the United States, now pending, and further claims priority benefits to Chinese Patent Application No. 201010244963.8 filed Aug. 4, 2010. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

1. Field of the Invention

This invention relates to a method for preparing a rosuvastatin calcium intermediate, and more particularly to a method for preparing a compound of formula I.

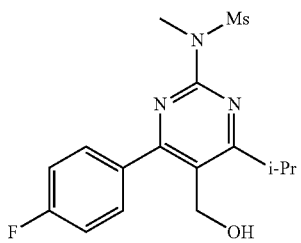

I

2. Description of the Related Art

Rosuvastatin calcium, with chemical name of (3R,5S,6E)-7-[4-(4-fluorophenyl)-6-isopropyl-2-(N-methyl-N-mesyl amino)-5-pyrimidine]-3,5-dihydroxyl-6-heptenoic acid calcium, is a new statin drug including a single enantiomer prepared by total synthesis, and belongs to HMG-CoA reductase inhibitors. Rosuvastatin calcium can lower rising LDL-cholesterol, total cholesterol, triglyceride, and apoprotein B, and increase HDL-cholesterol. Rosuvastatin calcium is used for comprehensive treatment of patients with primary hypercholesterolemia, combined hyperlipidemia, or homozygous familial hypercholesterolemia. Its chemical structural formula is as follows:

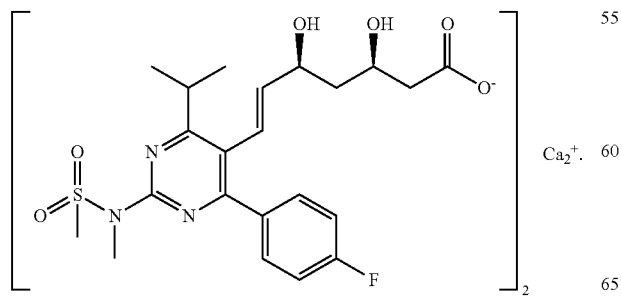

A typical preparation method of rosuvastatin calcium is as follows:

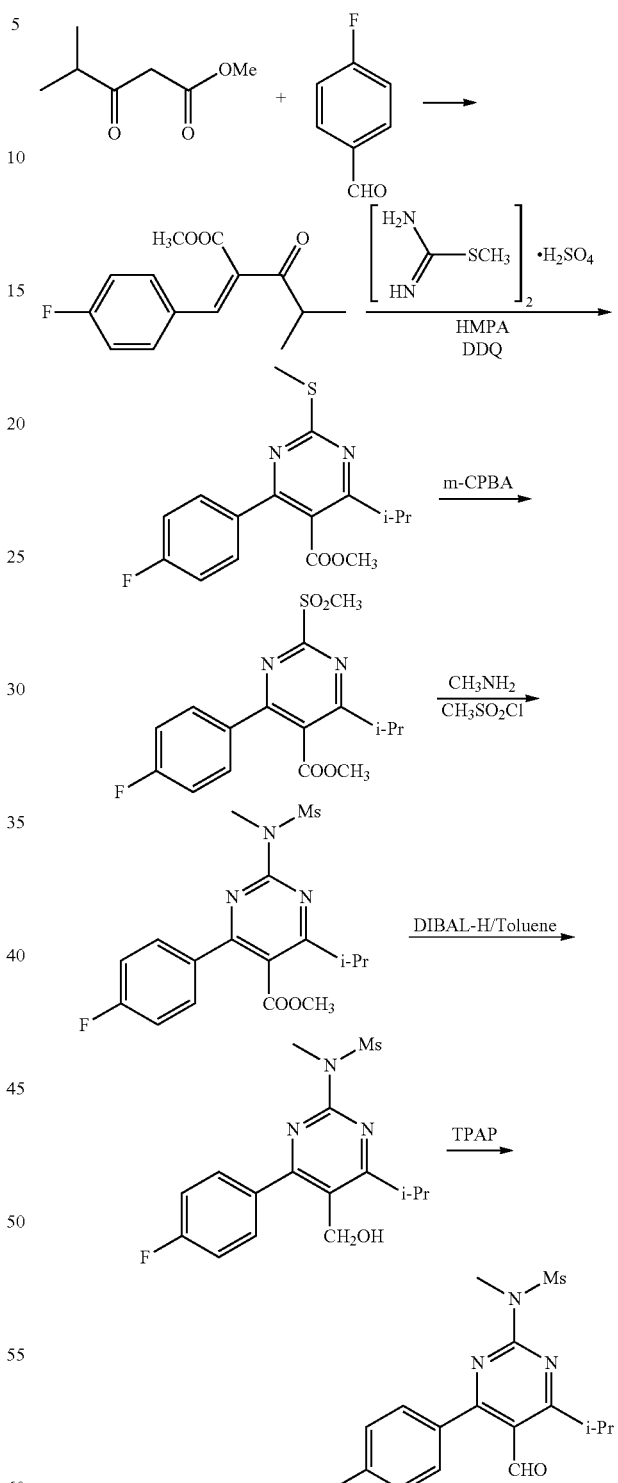

However, the method is disadvantageous in the following aspects: 1. DDQ (2,3-dichloro-5,6-dicyano-1,4-benzoquinone) is necessary in the process, but DDQ is extremely toxic; 2. Raw materials, such as 4-methylmorpholine-N-oxide, TPAP (tetrapropylammonium perruthenate), and DIBAL-H, are expensive; 3. DIBAL-H reacts at a low temperature about minus 70 degrees centigrade to minus 40 degrees centigrade, thereby resulting in a high energy consumption and production costs, which is not suitable for large-scale industrial production; and 4. The yield in the reaction is low.

SUMMARY OF THE INVENTION

In view of the above-described problems, it is one objective of the invention to provide a method for preparing a rosuvastatin calcium intermediate that is low in cost and suitable for industrial production.

To achieve the above objective, in accordance with one embodiment of the invention, there is provided a method for preparing a compound represented by formula I,

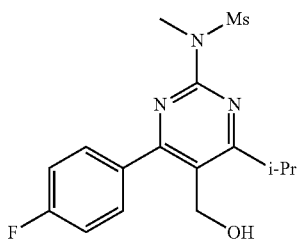

I the method comprising the following steps:
a) hydrolyzing an ester compound represented by formula II in the presence of a metallic compound to obtain a carboxylic acid compound represented by formula III,

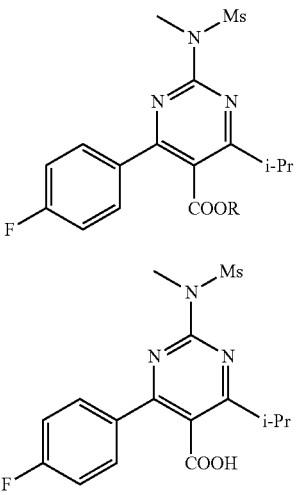

II

III in which, R represents a C1-C5 alkyl; and
b) reducing the carboxylic acid compound in the presence of a reductant to obtain the rosuvastatin calcium intermediate.

In a class of this embodiment, the metallic compound is LiOH or a hydrate thereof.

In a class of this embodiment, the reductant is a borane or a hydroboron and Lewis acid reduction system.

In a class of this embodiment, the hydroboron and Lewis acid reduction system is selected from the group consisting of a system comprising potassium borohydride and boron trifluoride diethyl etherate; a system comprising sodium borohydride and boron trifluoride diethyl etherate; a system comprising lithium borohydride and boron trifluoride diethyl etherate; a system comprising potassium borohydride and $H_2SO_4$; a system comprising potassium borohydride and $ZnCl_2$; a system comprising potassium borohydride and $AlCl_3$; a system comprising potassium borohydride and $I_2$; a system comprising potassium borohydride and $CF_3COOH$; a system comprising potassium borohydride and HCOOH; a system comprising potassium borohydride and MsOH; a system comprising potassium borohydride and $CH_3COOH$; a system comprising potassium borohydride and $NiCl_2$; a system comprising zinc borohydride and $H_2SO_4$; a system comprising zinc borohydride and $ZnCl_2$; a system comprising zinc borohydride and $AlCl_3$; a system comprising zinc borohydride and $I_2$; a system comprising zinc borohydride and $CF_3COOH$; a system comprising zinc borohydride and HCOOH; a system comprising zinc borohydride and MsOH; a system comprising zinc borohydride and $CH_3COOH$; a system comprising zinc borohydride and $NiCl_2$; a system comprising sodium borohydride and $H_2SO_4$; a system comprising sodium borohydride and $ZnCl_2$; a system comprising sodium borohydride and $AlCl_3$; a system comprising sodium borohydride and $I_2$; a system comprising sodium borohydride and $CF_3COOH$; a system comprising sodium borohydride and HCOOH; a system comprising sodium borohydride and MsOH; a system comprising sodium borohydride and $CH_3COOH$; a system comprising sodium borohydride and $NiCl_2$; a system comprising lithium borohydride and $H_2SO_4$; a system comprising lithium borohydride and $ZnCl_2$; a system comprising lithium borohydride and $AlCl_3$; a system comprising lithium borohydride and $I_2$; a system comprising lithium borohydride and $CF_3COOH$; a system comprising lithium borohydride and HCOOH; a system comprising lithium borohydride and MsOH; a system comprising lithium borohydride and $CH_3COOH$; and a system comprising lithium borohydride and $NiCl_2$.

Furthermore, the invention provides a compound represented by formula III, which is a new compound and is critical to achieve the method of the invention.

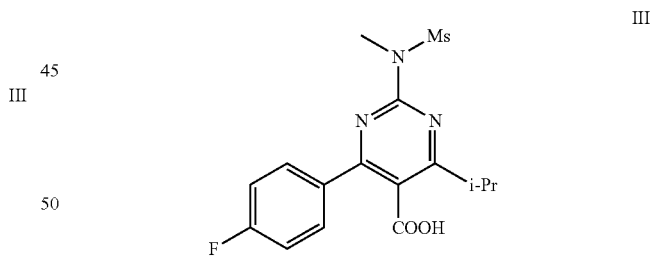

III

The compound represented by formula III has a fusion point of 211.0-212.35° C., and NMR data of the compound are as follows: 1HNMR (CDCl$_3$, 600 MHz): δ7.66-7.68 (m, 2H), δ7.06-7.09 (m, 2H), δ3.53 (s, 3H), δ3.45 (s, 3H), δ3.25-3.29 (m, 1H), δ1.28 (s, 3H), δ1.27 (s, 3H).

DETAILED DESCRIPTION OF THE EMBODIMENTS

For further illustrating the invention, experiments detailing a method for preparing a rosuvastatin calcium intermediate are described below. It should be noted that the following examples are intended to describe and not to limit the invention.

Example 1

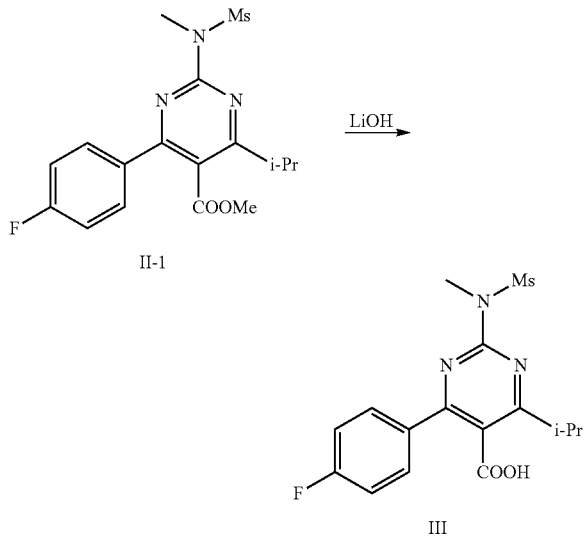

38.1 g of a compound represented by formula II-1 (HPLC: 99.5%), 3.2 g of LiOH, 150 g of pure water, and 150 g of tetrahydrofuran were added one after another into a 500 mL three mouth flask, stirred, and heated to a temperature of 60-70° C. for reaction. The reaction was monitored by thin-layer chromatography (TLC) until a complete reaction of the raw materials. Thereafter, a dissolvent was removed by vacuum distillation at a temperature of 30-35° C. and a vacuum degree of 250-350 Pa. Then, 150 mL of pure water was added to a remaining solid, PH value was adjusted to 2-3 by a diluted chlorohydric acid. After that, extraction was carried out three times with 600 mL of ethyl acetate. An organic phase was then washed by 100 mL of saturated salt water, and desiccated by anhydrous sodium sulfate. Thereafter, the organic phase was concentrated at the temperature of 30-35° C. and the vacuum degree of 250-350 Pa to obtain an off-white power, i.e., and a crude product of a compound represented by formula III. The crude product was recrystallized by methyl tert-butyl ether to obtain 33.2 g of a white crystalline solid, its purity detected by HPLC was 99.5%, and its yield was 90.5%.

NMR data of the compound represented by formula III were as follows: 1HNMR (CDCl$_3$, 600 MHz): δ7.66-7.68 (m, 2H), δ7.06-7.09 (m, 2H), δ3.53 (s, 3H), δ3.45 (s, 3H), δ3.25-3.29 (m, 1H), δ1.28 (s, 3H), δ1.27 (s, 3H).

Example 2

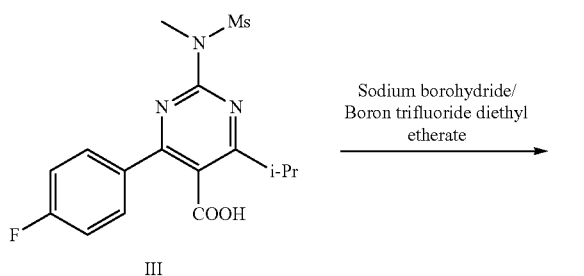

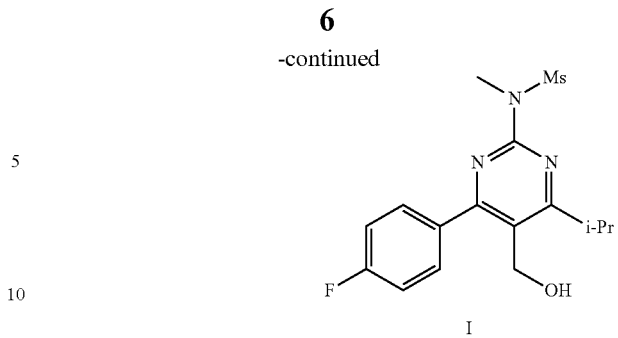

70 mL of tetrahydrofuran and 2.2 g of sodium borohydride were added into a 500 mL three mouth flask, a temperature was lowered to between −5 and 5° C. 18 g of boron trifluoride diethyl etherate was slowly dripped into the flask while stirring. After stirring for 30 min-1 h, 7.2 g of a compound represented by formula III (HPLC: 99.5%) was added at the temperature of between −5 and 5° C. The temperature was kept at between −5 and 5° C. for 2-4 h for reaction, then, the temperature was increased to 20-30° C. for reaction. After a complete reaction of the compound represented by formula III, methanol was slowly dripped for quenching the reaction. Thereafter, vacuum distillation was carried out at a temperature of 30-35° C. and a vacuum degree of 250-350 Pa to remove a dissolvent; then, a remaining solid was added with 40 mL of water and stirred, PH value was adjusted to 2-3. After that, extraction was carried out three times with 200 mL of methyl tert-butyl ether. A vacuum concentration was carried out at the temperature of 30-35° C. and the vacuum degree of 250-350 Pa to obtain a white solid, i.e., a crude product of a compound represented by formula I. The crude product was recrystallized by a mixture of methyl tert-butyl ether and n-hexane (1:10 of a volume ratio) to obtain 6.7 g of a product, its purity was 99.0%, and its yield was 96.4%.

Example 3

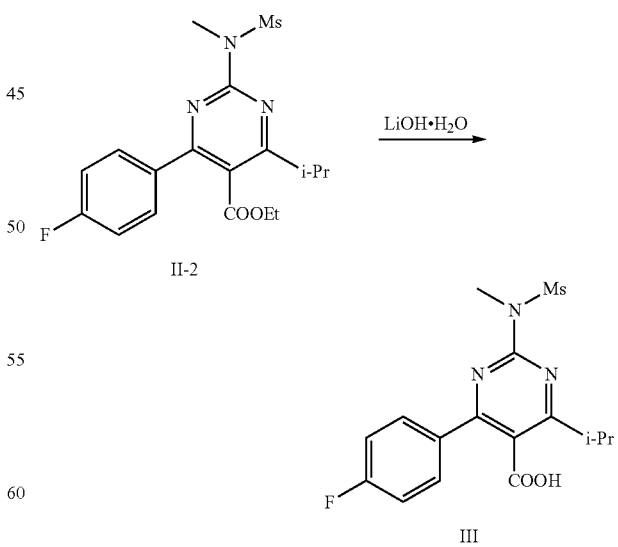

39.5 g of a compound represented by formula II-2 (HPLC: 99.5%), 4.6 g of LiOH.H$_2$O, 150 g of pure water, and 130 g of methanol were added one after another into a 500 mL three mouth flask, stirred, and heated to a temperature of 60-70° C.

for reaction. The reaction was monitored by TLC until a complete reaction of the raw materials. Thereafter, a dissolvent was removed by vacuum distillation at a temperature of 30-35° C. and a vacuum degree of 250-350 Pa. Then, 150 mL of pure water was added to a remaining solid, PH value was adjusted to 2-3 by a diluted chlorohydric acid. After that, extraction was carried out three times with 600 mL of ethyl acetate. An organic phase was then washed by 100 mL of saturated salt water, and desiccated by anhydrous sodium sulfate. Thereafter, the organic phase was concentrated at the temperature of 30-35° C. and the vacuum degree of 250-350 Pa to obtain an off-white power, i.e., and a crude product of a compound represented by formula III. The crude product was recrystallized by methyl tert-butyl ether to obtain 32.9 g of a white crystalline solid, its purity detected by HPLC was 99.4%, and its yield was 89.6%.

Example 4

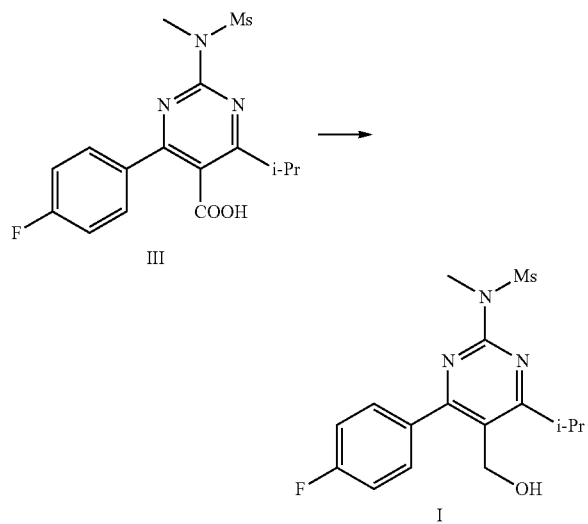

70 mL of tetrahydrofuran and 3.1 g of potassium borohydride were added into a 500 mL three mouth flask, a temperature was lowered to between −5 and 5° C. 18 g of boron trifluoride diethyl etherate was slowly dripped into the flask while stirring. After stirring for 30 min-1 h, 7.2 g of a compound represented by formula III (HPLC: 99.4%) was added at the temperature of between −5 and 5° C. The temperature was kept at between −5 and 5° C. for 2-4 h for reaction, then, the temperature was increased to 15-25° C. for reaction. After a complete reaction of the compound represented by formula III, methanol was slowly dripped for quenching the reaction. Thereafter, vacuum distillation was carried out at a temperature of 30-35° C. and a vacuum degree of 250-350 Pa to remove a dissolvent; then, a remaining solid was added with 40 mL of water and stirred, PH value was adjusted to 2-3. After that, extraction was carried out three times with 200 mL of methyl tert-butyl ether. A vacuum concentration was carried out at the temperature of 30-35° C. and the vacuum degree of 250-350 Pa to obtain a white solid, i.e., a crude product of a compound represented by formula I. The crude product was recrystallized by a mixture of methyl tert-butyl ether and n-hexane (1:10 of a volume ratio) to obtain 6.6 g of a product, its purity was 99.3%, and its yield was 95.2%.

Example 5

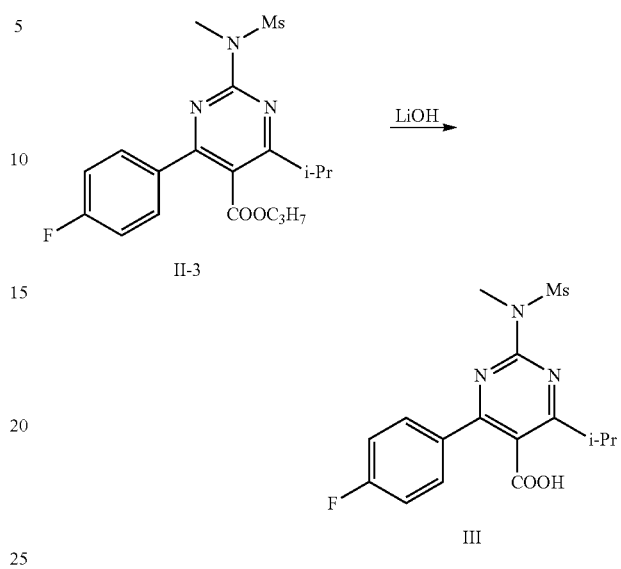

40.9 g of a compound represented by formula II-3 (HPLC: 99.5%), 3.3 g of LiOH, 150 g of pure water, and 130 g of 1,4-dioxane were added one after another into a 500 mL three mouth flask, stirred, and heated to a temperature of 60-70° C. for reaction. The reaction was monitored by TLC until a complete reaction of the raw materials. Thereafter, a dissolvent was removed by vacuum distillation at a temperature of 30-35° C. and a vacuum degree of 250-350 Pa. Then, 150 mL of pure water was added to a remaining solid, PH value was adjusted to 2-3 by a diluted chlorohydric acid. After that, extraction was carried out three times with 600 mL of ethyl acetate. An organic phase was then washed by 100 mL of saturated salt water, and desiccated by anhydrous sodium sulfate. Thereafter, the organic phase was concentrated at the temperature of 30-35° C. and the vacuum degree of 250-350 Pa to obtain an off-white power, i.e., and a crude product of a compound represented by formula III. The crude product was recrystallized by methyl tert-butyl ether to obtain 33.0 g of a white crystalline solid, its purity detected by HPLC was 99.2%, and its yield was 89.7%.

Example 6

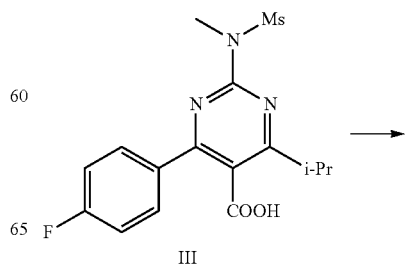

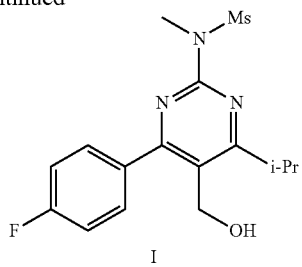

I 70 mL of tetrahydrofuran and 1.3 g of lithium borohydride were added into a 500 mL three mouth flask, a temperature was lowered to between −5 and 5° C. 18 g of boron trifluoride diethyl etherate was slowly dripped into the flask while stirring. After stirring for 30 min-1 h, 7.2 g of a compound represented by formula III (HPLC: 99.2%) was added at the temperature of between −5 and 5° C. The temperature was kept at between −5 and 5° C. for 2-4 h for reaction, then, the temperature was increased to 10-20° C. for reaction. After a complete reaction of the compound represented by formula III, methanol was slowly dripped for quenching the reaction. Thereafter, vacuum distillation was carried out at a temperature of 30-35° C. and a vacuum degree of 250-350 Pa to remove a dissolvent; then, a remaining solid was added with 40 mL of water and stirred, PH value was adjusted to 2-3. After that, extraction was carried out three times with 200 mL of methyl tert-butyl ether. A vacuum concentration was carried out at the temperature of 30-35° C. and the vacuum degree of 250-350 Pa to obtain a white solid, i.e., a crude product of a compound represented by formula I. The crude product was recrystallized by a mixture of methyl tert-butyl ether and n-hexane (1:10 of a volume ratio) to obtain 6.8 g of a product, its purity was 99.0%, and its yield was 97.8%.

Example 7

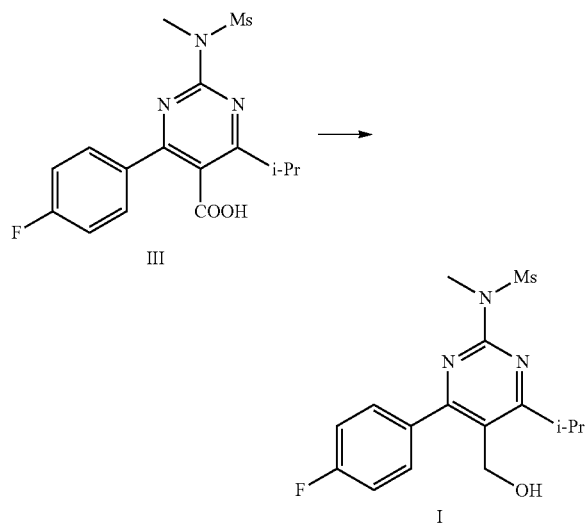

70 mL of tetrahydrofuran and 3.3 g of potassium borohydride were added into a 500 mL three mouth flask, a temperature was lowered to between −5 and 5° C. 50 g of concentrated sulfuric acid was slowly dripped into the flask while stirring. After stirring for 30 min-1 h, 7.2 g of a compound represented by formula III (HPLC: 99.2%) was added at the temperature of between −5 and 5° C. The temperature was kept at between −5 and 5° C. for 2-4 h for reaction, then, the temperature was increased to 10-20° C. for reaction. After a complete reaction of the compound represented by formula III, methanol was slowly dripped for quenching the reaction. Thereafter, vacuum distillation was carried out at a temperature of 30-35° C. and a vacuum degree of 250-350 Pa to remove a dissolvent; then, a remaining solid was added with 40 mL of water and stirred, PH value was adjusted to 2-3. After that, extraction was carried out three times with 200 mL of methyl tert-butyl ether. A vacuum concentration was carried out at the temperature of 30-35° C. and the vacuum degree of 250-350 Pa to obtain an off-white solid, i.e., a crude product of a compound represented by formula I. The crude product was recrystallized by a mixture of methyl tert-butyl ether and n-hexane (1:10 of a volume ratio) to obtain 6.5 g of a product, its purity was 99.3%, and its yield was 93.8%.

Example 8

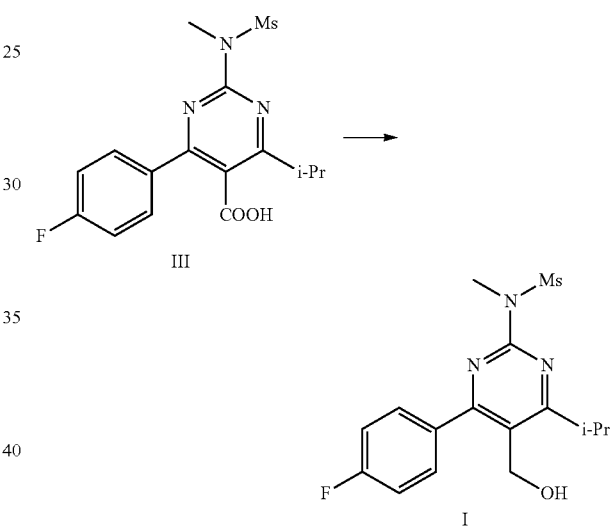

70 mL of tetrahydrofuran and 3.3 g of potassium borohydride were added into a 500 mL three mouth flask, a temperature was lowered to between −5 and 5° C. 33.3 g of zinc chloride was slowly dripped into the flask while stirring. After stirring for 30 min-1 h, 7.2 g of a compound represented by formula III (HPLC: 99.2%) was added at the temperature of between −5 and 5° C. The temperature was kept at between −5 and 5° C. for 2-4 h for reaction, then, the temperature was increased to 10-20° C. for reaction. After a complete reaction of the compound represented by formula III, methanol was slowly dripped for quenching the reaction. Thereafter, vacuum distillation was carried out at a temperature of 30-35° C. and a vacuum degree of 250-350 Pa to remove a dissolvent; then, a remaining solid was added with 40 mL of water and stirred, PH value was adjusted to 2-3. After that, extraction was carried out three times with 200 mL of methyl tert-butyl ether. A vacuum concentration was carried out at the temperature of 30-35° C. and the vacuum degree of 250-350 Pa to obtain an off-white solid, i.e., a crude product of a compound represented by formula I. The crude product was recrystallized by a mixture of methyl tert-butyl ether and n-hexane (1:10 of a volume ratio) to obtain 6.6 g of a product, its purity was 99.1%, and its yield was 95.1%.

Example 9

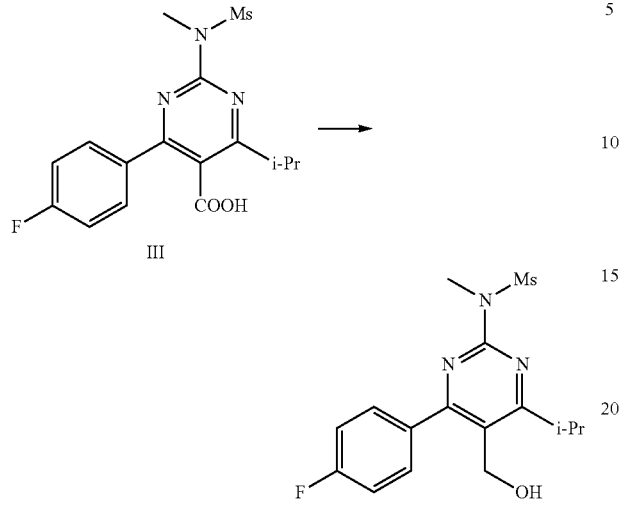

70 mL of tetrahydrofuran and 3.3 g of potassium borohydride were added into a 500 mL three mouth flask, a temperature was lowered to between −5 and 5° C. 32.6 g of zinc chloride was slowly dripped into the flask while stirring. After stirring for 30 min-1 h, 7.2 g of a compound represented by formula III (HPLC: 99.2%) was added at the temperature of between −5 and 5° C. The temperature was kept at between −5 and 5° C. for 3-5 h for reaction, then, the temperature was increased to 10-20° C. for reaction. After a complete reaction of the compound represented by formula III, methanol was slowly dripped for quenching the reaction. Thereafter, vacuum distillation was carried out at a temperature of 30-35° C. and a vacuum degree of 250-350 Pa to remove a dissolvent; then, a remaining solid was added with 40 mL of water and stirred, PH value was adjusted to 2-3. After that, extraction was carried out three times with 200 mL of methyl tert-butyl ether. A vacuum concentration was carried out at the temperature of 30-35° C. and the vacuum degree of 250-350 Pa to obtain an off-white solid, i.e., a crude product of a compound represented by formula I. The crude product was recrystallized by a mixture of methyl tert-butyl ether and n-hexane (1:10 of a volume ratio) to obtain 6.6 g of a product, its purity was 99.2%, and its yield was 95.2%.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing a compound represented by formula I,

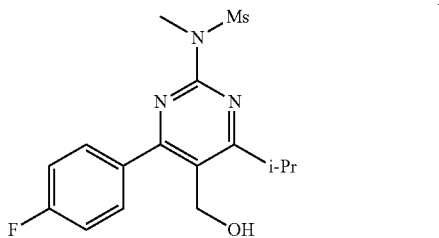

the method comprising the following steps:
a) hydrolyzing an ester compound represented by formula II in the presence of a metallic compound to obtain a carboxylic acid compound represented by formula III,

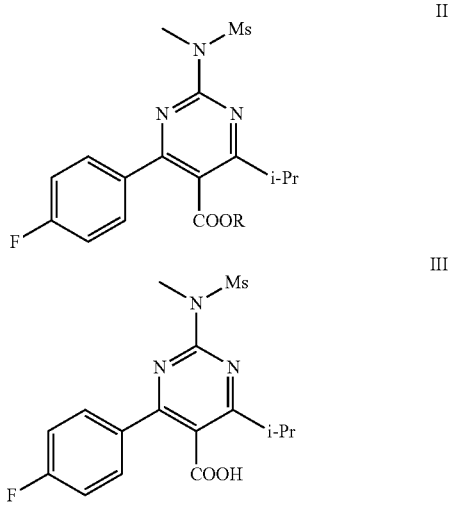

in which, R represents a C1-C5 alkyl; and
b) reducing the carboxylic acid compound in the presence of a reductant.

2. The method of claim 1, wherein in step a), the metallic compound is LiOH or a hydrate thereof.

3. The method of claim 1, wherein in step b), the reductant is a borane or a hydroboron and Lewis acid reduction system.

4. The method of claim 3, wherein the hydroboron and Lewis acid reduction system is selected from the group consisting of a system comprising potassium borohydride and boron trifluoride diethyl etherate; a system comprising sodium borohydride and boron trifluoride diethyl etherate; a system comprising lithium borohydride and boron trifluoride diethyl etherate; a system comprising potassium borohydride and $H_2SO_4$; a system comprising potassium borohydride and $ZnCl_2$; a system comprising potassium borohydride and $AlCl_3$; a system comprising potassium borohydride and $I_2$; a system comprising potassium borohydride and $CF_3COOH$; a system comprising potassium borohydride and HCOOH; a system comprising potassium borohydride and MsOH; a system comprising potassium borohydride and $CH_3COOH$; a system comprising potassium borohydride and $NiCl_2$; a system comprising zinc borohydride and $H_2SO_4$; a system comprising zinc borohydride and $ZnCl_2$; a system comprising zinc borohydride and $AlCl_3$; a system comprising zinc borohydride and $I_2$; a system comprising zinc borohydride and $CF_3COOH$; a system comprising zinc borohydride and HCOOH; a system comprising zinc borohydride and MsOH; a system comprising zinc borohydride and CH₃COOH; a system comprising zinc borohydride and NiCl₂; a system comprising sodium borohydride and H₂SO₄; a system comprising sodium borohydride and ZnCl₂; a system comprising sodium borohydride and AlCl₃; a system comprising sodium borohydride and I₂; a system comprising sodium borohydride and CF₃COOH; a system comprising sodium borohydride and HCOOH; a system comprising sodium borohydride and MsOH; a system comprising sodium borohydride and CH₃COOH; a system comprising sodium borohydride and NiCl₂; a system comprising lithium borohydride and H₂SO₄; a system comprising lithium borohydride and ZnCl₂; a system comprising lithium borohydride and AlCl₃; a system comprising lithium borohydride and I₂; a system comprising lithium borohydride and CF₃COOH; a system comprising lithium borohydride and HCOOH; a system comprising lithium borohydride and MsOH; a system comprising lithium borohydride and CH₃COOH; and a system comprising lithium borohydride and NiCl₂.

5. A compound represented by formula III:

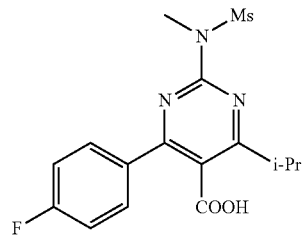

* * * * *